US009089272B2

(12) United States Patent
Thakur et al.

(10) Patent No.: US 9,089,272 B2
(45) Date of Patent: Jul. 28, 2015

(54) ESTIMATING RESTITUTION CURVES IN AN ANATOMICAL MAPPING SYSTEM

(71) Applicant: Boston Scientific Scimed, Inc., Maple Grove, MN (US)

(72) Inventors: Pramodsingh H. Thakur, Woodbury, MN (US); Barun Maskara, Blaine, MN (US); Shantha Arcot-Krishnamurthy, Renton, WA (US); Shibaji Shome, Arden Hills, MN (US); Sunipa Saha, Shoreview, MN (US); Allan C. Shuros, St. Paul, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 14/133,242

(22) Filed: Dec. 18, 2013

(65) Prior Publication Data

US 2014/0187989 A1 Jul. 3, 2014

Related U.S. Application Data

(60) Provisional application No. 61/748,181, filed on Jan. 2, 2013.

(51) Int. Cl.
*A61B 5/04* (2006.01)
*A61B 5/0452* (2006.01)
(Continued)

(52) U.S. Cl.
CPC .............. *A61B 5/0452* (2013.01); *A61B 5/0422* (2013.01); *A61B 5/6858* (2013.01); *A61B 5/04012* (2013.01); *A61B 18/1492* (2013.01); *A61B 2018/00357* (2013.01); *A61B 2018/00577* (2013.01)

(58) Field of Classification Search
USPC .......................................................... 600/509
See application file for complete search history.

(56) References Cited

U.S. PATENT DOCUMENTS 5,647,870 A 7/1997 Kordis et al.
6,070,094 A 5/2000 Swanson et al.
(Continued)

FOREIGN PATENT DOCUMENTS

WO WO2012151301 A1 11/2012

OTHER PUBLICATIONS

Conrath et al., Ventricular Repolarization: An Overview of (Patho)physiology, Sympathetic Effects and Genetic Aspects, Progress in Biophysics and Molecular Biology, vol. 92, No. 3, Nov. 1, 2006, 39 pgs.

(Continued)

*Primary Examiner* — Robert N Wieland
(74) *Attorney, Agent, or Firm* — Faegre Baker Daniels LLP

(57) ABSTRACT

A method for mapping an anatomical structure includes sensing activation signals of physiological activity with a plurality of electrodes disposed in or near the anatomical structure, each activation signal having an associated cycle length, estimating an action potential duration and diastolic interval for each cycle length, generating a restitution curve based on the estimated action potential duration and diastolic interval from a preceding cycle length, iteratively optimizing each estimated action potential duration and corresponding diastolic interval to maximize a functional relationship between the estimated action potential duration and estimated diastolic interval from preceding cycle length, and generating an action potential duration restitution curve based on the optimized action potential durations and diastolic intervals.

30 Claims, 6 Drawing Sheets

(51) Int. Cl.
*A61B 5/00* (2006.01)
*A61B 5/042* (2006.01)
*A61B 18/14* (2006.01)
*A61B 18/00* (2006.01)

(56) References Cited

U.S. PATENT DOCUMENTS

| | | | |
|---|---|---|---|
| 6,094,593 | A | 7/2000 | Karagueuzian et al. |
| 6,233,491 | B1 | 5/2001 | Kordis et al. |
| 6,735,465 | B2 | 5/2004 | Panescu |
| 6,993,388 | B2 | 1/2006 | Bullinga |
| 2009/0299424 | A1 | 12/2009 | Narayan |
| 2010/0094274 | A1 | 4/2010 | Narayan et al. |
| 2013/0006131 | A1* | 1/2013 | Narayan et al. ............... 600/508 |

OTHER PUBLICATIONS

International Search Report and Written Opinion issued in PCT/US2013/077143, mailed Mar. 4, 2014, 10 pgs.

Rogers, Modeling the Cardiac Action Potential Using B-Spline Surfaces, IEEE Transactions on Biomedical Engineering, vol. 47, No. 6, Jun. 1, 2000, 8 pgs.

Schaeffer et al., An Ionically Based Mapping Model with Memory for Cardiac Restitution, Bulletin of Mathematical Biology, vol. 69, No. 2. Jan. 20, 2007, 24 pgs.

Yu et al., Global Endocardial Electrical Restitution in Human Right and Left Ventricles Determined by Noncontact Mapping, Journal of the American College of Cardiology, vol. 46, No. 6, Sep. 20, 2005, 9 pgs.

* cited by examiner

ESTIMATING RESTITUTION CURVES IN AN ANATOMICAL MAPPING SYSTEM

CROSS-REFERENCE TO RELATED APPLICATIONS

This application claims the benefit under 35 U.S.C. section 119(e) to U.S. Provisional Application 61/748,181, entitled "ESTIMATING RESTITUTION CURVES IN AN ANATOMICAL MAPPING SYSTEM", filed on Jan. 2, 2013, which is herein incorporated by reference in its entirety.

TECHNICAL FIELD

The present disclosure relates to cardiac mapping systems. More specifically, the present disclosure relates to a cardiac mapping system configured to estimate restitution curves based on recorded activation signals.

BACKGROUND

Electrical restitution is the relationship between changes in action potential duration with varying diastolic intervals occurring between a first cardiac systole and an extra systole. Restitution reflects the recovery properties of the cardiac tissue with respect to the time of initiation of the extra systole. An electrical restitution curve can be constructed by measuring the action potential duration over a range of diastolic intervals. The curve is initially very steep where short diastolic intervals result in a greater shortening of the action potential durations. After the initially steep portion, a plateau is reached as the action potential duration (APD) reaches a maximum at longer diastolic intervals. The slope of the electrical restitution curve over the entire range of diastolic intervals or the slope of the steepest portion of the curve can be used as a measure of the responsiveness of APD changes to a change in diastolic interval. Increased dispersion of action potential duration and refractoriness is associated with an increased risk of arrhythmias. The shortened action potential duration resulting from the shortened diastolic interval alters the refractoriness of the myocardium which is believed to set up pathways for reentrant depolarizations in a way that greatly enhances susceptibility to fibrillation.

SUMMARY

Disclosed herein are various embodiments of a method for mapping anatomical structures from intrinsic cardiac activation signals sensed by a cardiac catheter, as well as anatomical mapping systems employing such methods.

In Example 1, a method for mapping an anatomical structure includes sensing activation signals of physiological activity with a plurality of electrodes disposed in or near the anatomical structure, each activation signal having an associated cycle length, estimating an action potential duration and diastolic interval for each cycle length, generating an initial restitution curve based on the estimated action potential duration and diastolic interval from a preceding cycle length, iteratively optimizing each estimated action potential duration and corresponding diastolic interval to maximize a functional relationship between the estimated action potential duration and estimated diastolic interval from preceding cycle length, and generating a final action potential duration restitution curve based on the optimized action potential durations and diastolic intervals.

In Example 2, the method according to Example 1, wherein the step of estimating an action potential duration and diastolic interval includes randomly partitioning each cycle length to estimate the corresponding action potential duration and diastolic interval.

In Example 3, the method according to either Example 1 or 2, wherein the step of iteratively optimizing each estimated action potential duration and corresponding diastolic interval further includes iteratively optimizing with a first partition resolution, and iteratively optimizing with a second partition resolution after optimizing with the first partition resolution, wherein the second partition resolution is higher than the first partition resolution.

In Example 4, the method according to any of Examples 1-3, wherein the step of generating the restitution curve includes generating a two-dimensional dataset that pairs each estimated action potential duration with the estimated diastolic interval from a preceding cycle length, and plotting the two-dimensional dataset to generate an initial restitution curve.

In Example 5, the method according to any of Examples 1-4, wherein the step of maximizing the functional relationship includes at least one of maximizing a mutual information between the estimated action potential duration and estimated diastolic interval from preceding cycle length, maximizing a maximal information coefficient score the estimated action potential duration and estimated diastolic interval from preceding cycle length, and maximizing a distance correlation measure between the estimated action potential duration and estimated diastolic interval from preceding cycle length.

In Example 6, the method according to any of Examples 1-5, the method further includes maximizing a similarity between the generated restitution curve and a predetermined restitution template.

In Example 7, the method according to any of Examples 1-6, wherein the step of maximizing the similarity includes at least one of maximizing a correlation coefficient between the generated restitution curve and the predetermined restitution template, and minimizing a mean square error between the generated restitution curve and the predetermined restitution template.

In Example 8, the method according to any of Examples 1-7, wherein the predetermined restitution template corresponds to any one of an exponential function, a sigmoidal function, and a previously generated optimized restitution curve.

In Example 9, the method according to any of Examples 1-8, wherein the action potential duration restitution curve is generated for each of the plurality of electrodes.

In Example 10, the method according to any of Examples 1-9, wherein the activation signals of physiological activity are sensed in response to a pre-determined pacing protocol instituted by at least one of the plurality of electrodes.

In Example 11, the method according to any of Examples 1-10, the method further includes generating an anatomical map of the anatomical structure based on the generated action potential duration restitution curve.

In Example 12, a method for mapping an anatomical structure includes sensing cardiac activation signals with a plurality of electrodes disposed in or near the anatomical structure, each activation signal associated with a cycle length, partitioning each cycle length into an action potential duration and a diastolic interval, generating a restitution dataset such that each data point includes an action potential duration and a directly preceding diastolic interval, generating a two-dimensional plot of the data points, the plot having a predefined grid of discrete grid locations, determining a functional association within the restitution dataset, adjusting the partition of each cycle length such that each data point is shifted from one grid location to another grid location, repeating the adjusting and determining steps to maximize the functional association within the restitution data set, and generating an action potential duration restitution curve based on the restitution dataset corresponding to the maximized functional association.

In Example 13, the method according to Examples 12, wherein the functional association includes at least one of maximizing a mutual information between the estimated action potential duration and estimated diastolic interval from preceding cycle length, maximizing a maximal information coefficient score the estimated action potential duration and estimated diastolic interval from preceding cycle length, and maximizing a distance correlation measure between the estimated action potential duration and estimated diastolic interval from preceding cycle length.

In Example 14, the method according to either of Examples 12 and 13, wherein the functional association is based on maximizing a similarity between the generated restitution curve and a predetermined restitution template.

In Example 15, the method according to any of Examples 12-14, wherein the similarity includes at least one of maximizing a correlation coefficient between the generated restitution curve and the predetermined restitution template, and minimizing a mean square error between the generated restitution curve and the predetermined restitution template.

In Example 16, the method according to any of Examples 12-15, wherein the predetermined restitution template corresponds to any one of an exponential function, a sigmoidal function, and a previously generated optimized restitution curve.

In Example 17, the method according to any of Examples 12-16, wherein after the functional association is maximized, the method includes increasing the resolution of the pre-defined grid, and repeating the adjusting and determining steps until the functional association is further increased across the entire restitution data set.

In Example 18, the method according to any of Examples 12-17, wherein the cardiac activation signals are sensed in response to a pre-determined pacing protocol instituted by at least one of the plurality of electrodes.

In Example 19, the method according to any of Examples 12-18, wherein the predetermined pacing protocol includes at least one of random pacing pulses with inter-pulse intervals sampled from a statistical distribution.

In Example 20, the method according to any of Examples 12-19, the method further including generating a cardiac map based on the generating action potential duration restitution curve.

In Example 21, a method for mapping an anatomical structure includes sensing activation signals of physiological activity with a plurality of electrodes disposed in or near the anatomical structure, each activation signal having an associated cycle length, generating a function of action potential duration and preceding cycle length, partitioning each cycle length into an action potential duration and a diastolic interval based on the generated function, and generating an action potential duration restitution curve based on the partitioned action potential duration and a preceding diastolic interval.

In Example 22, the method according to Example 21, wherein the step of generating a function includes generating a histogram of the cycle length of each activation signal based on the preceding cycle length, determining a refractory period of a cycle length based on the generated histogram, estimating an action potential duration based on the determined refractory period, and repeating the steps of generating a histogram, determining the refractory period, and estimating the action potential duration for a plurality of preceding cycle length.

In Example 23, the method according to either of Examples 20-21, wherein the step of generating a histogram includes determining the range of recorded cycle lengths, segmenting the determined range into equidistance bins, identifying all triplets of three consecutive activation signals, and generating a histogram of cycle lengths for a second and third activation signal for triplets that share a first cycle length bin.

In Example 24, the method according to any of Examples 20-23, wherein the refractory period is determined for all cycle length bins.

In Example 25, the method according to any of Examples 20-24, wherein the step of determining the refractory period includes identifying a region of the generated histogram between zero and a first bin with counts at least equal to a predetermined threshold, and determining the refractory period according to the identified region.

In Example 26, the method according to any of Examples 20-25, wherein the estimated action potential duration is the duration of the refractory period.

In Example 27, the method according to any of Examples 20-26, wherein the step of determining the refractory period includes fitting a smoothing function to the generated histogram, and identifying as the refractory period a region of the generated histogram between zero and where the smoothing function falls below a predetermined threshold.

In Example 28, the method according to any of Examples 20-27, wherein the smoothing function is a sigmoidal smoothing function.

In Example 29, the method according to any of Examples 20-28, wherein the activation signals of physiological activity are sensed in response to a pre-determined pacing protocol instituted by at least one of the plurality of electrodes.

In Example 30, the method according to any of Examples 20-29, the method further includes generating a cardiac map based on the generating action potential duration restitution curve.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
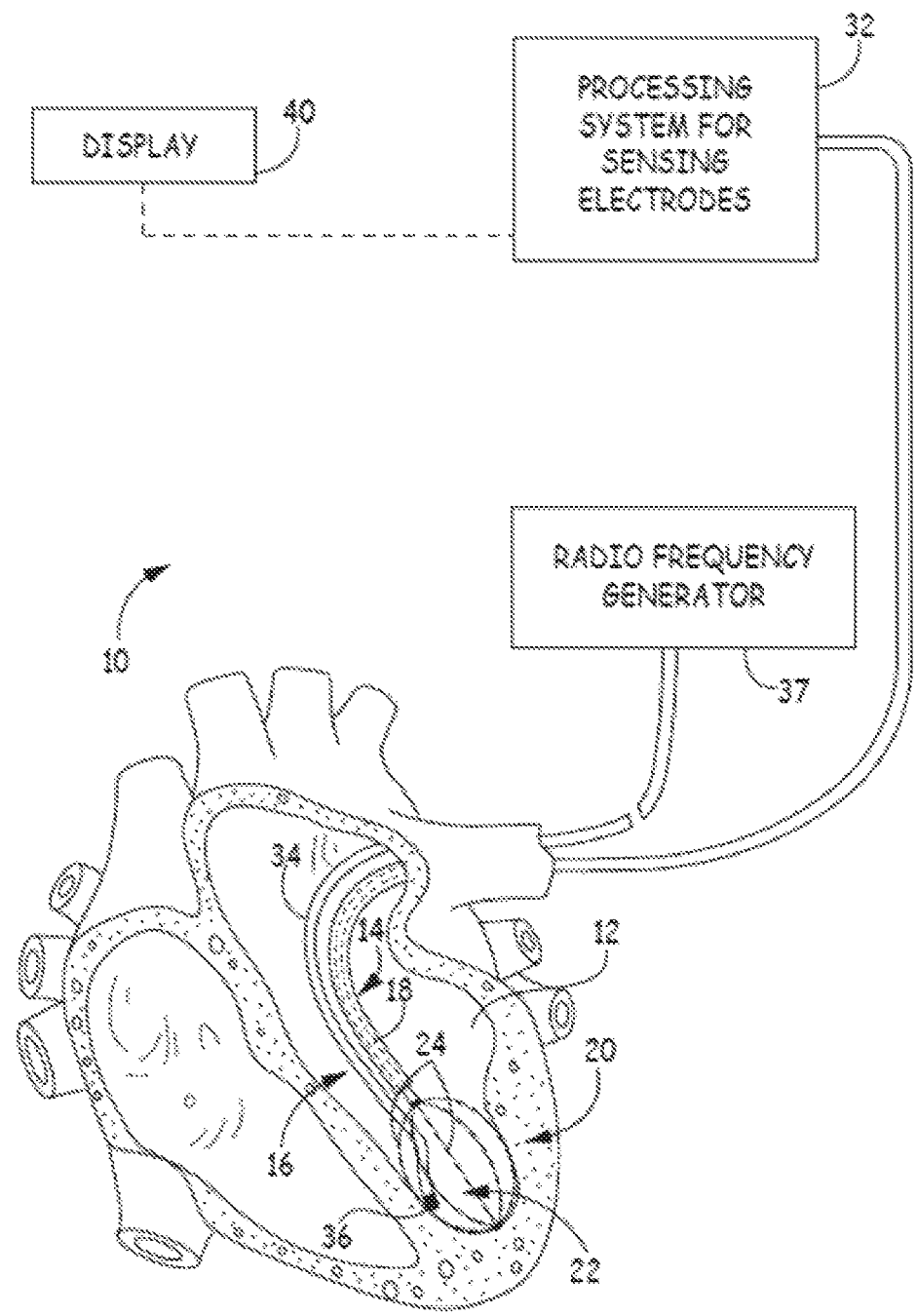
FIG. 1 a schematic view of an embodiment of a catheter system for accessing a targeted tissue region in the body for diagnostic and therapeutic purposes.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a system 10 for accessing a targeted tissue region in the body for diagnostic or therapeutic purposes. FIG. 1 generally shows the system 10 deployed in the left ventricle of the heart. Alternatively, system 10 can be deployed in other regions of the heart, such as the left atrium, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, and other regions of the body, including in systems that are not necessarily catheter-based.

The system 10 includes a mapping probe 14 and an ablation probe 16. In FIG. 1, each is separately introduced into the selected heart region 12 through a vein or artery (e.g., the femoral vein or artery) through suitable percutaneous access. Alternatively, the mapping probe 14 and ablation probe 16 can be assembled in an integrated structure for simultaneous introduction and deployment in the heart region 12.

The mapping probe 14 has a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used wherein the geometry of the electrode structure and electrode locations are known. The multiple electrode structure 20 carries a plurality of mapping electrodes 24 each having an electrode location and channel. Each electrode 24 is configured to sense intrinsic physiological activity in the anatomical region on which the ablation procedure is to be performed. In some embodiments, the electrodes are configured to detect activation signals of the intrinsic physiological activity within the anatomical structure, e.g., the activation times of cardiac activity.

The electrodes 24 are electrically coupled to a processing system 32. A signal wire (not shown) is electrically coupled to each electrode 24 on the basket structure 20. The wires extend through the body 18 of the probe 14 and electrically couple each electrode 24 to an input of the processing system 32, as will be described later in greater detail. The electrodes 24 sense intrinsic electrical activity in the anatomical region, e.g., myocardial tissue. The sensed activity, e.g. activation signals, is processed by the processing system 32 to assist the physician by generating an anatomical map, e.g. action potential duration (APD) restitution curve or a conduction velocity (CV) restitution curve, to identify the site or sites within the heart appropriate for ablation.

The ablation probe 16 includes a flexible catheter body 34 that carries one or more ablation electrodes 36. The one or more ablation electrodes 36 are electrically connected to a radio frequency (RF) generator 37 that is configured to deliver ablation energy to the one or more ablation electrodes 36. The ablation probe 16 is movable with respect to the anatomical feature to be treated, as well as the structure 20. The ablation probe 16 is positionable between or adjacent to electrodes 24 of the structure 20 as the one or more ablation electrodes 36 are positioned with respect to the tissue to be treated.

The processing system 32 outputs to a display 40 the generated APD map to the physician. In the illustrated embodiment, the processing system 32 includes an output display device 40 (e.g., a CRT, LED display, or a printer). The device 40 presents the APD map in a format most useful to the physician. In addition, the processing system 32 may generate position-identifying output for display on the display device 40 that aids the physician in guiding the ablation electrode(s) 36 into contact with tissue at the site identified for ablation.

Figure 2:
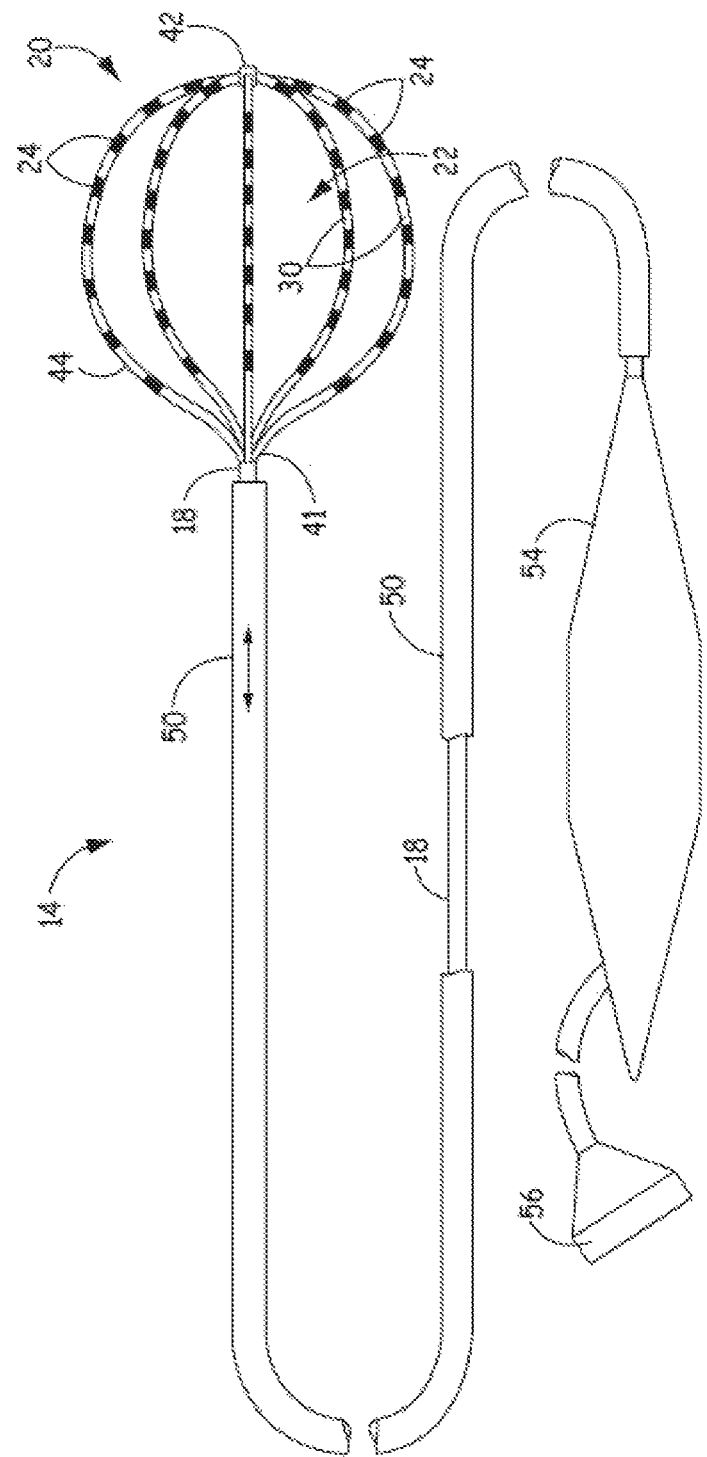
FIG. 2 is a schematic view of an embodiment of a mapping catheter having a basket functional element carrying structure for use in association with the system of FIG. 1.

FIG. 2 illustrates an embodiment of the mapping catheter 14 including electrodes 24 at the distal end suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity, e.g. activation signals, in the myocardial tissue, the sensed activity is then processed by the processing system 32 to assist the physician in identifying the site or sites having a heart rhythm disorder or other myocardial pathology via a generated and displayed APD restitution curve. This process is commonly referred to as mapping. This information can then be used to determine an appropriate location for applying appropriate therapy, such as ablation, to the identified sites, and to navigate the one or more ablation electrodes 36 to the identified sites.

The illustrated three-dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is larger (e.g., 40 mm in diameter or greater).

A slidable sheath 50 is movable along the major axis of the catheter body 30. Moving the sheath 50 forward (i.e., toward the distal end) causes the sheath 50 to move over the three dimensional structure 20, thereby collapsing the structure 20 into a compact, low profile condition suitable for introduction into an interior space, such as, for example, into the heart. In contrast, moving the sheath 50 rearward (i.e., toward the proximal end) exposes the three dimensional structure 20, allowing the structure 20 to elastically expand and assume the pretensed position illustrated in FIG. 2. Further details of embodiments of the three dimensional structure 20 are disclosed in U.S. Pat. No. 5,647,870, entitled "Multiple Electrode Support Structures," which is hereby incorporated by reference in its entirety.

A signal wire (not shown) is electrically coupled to each mapping electrode 26. The wires extend through the body 30 of the mapping catheter 20 into a handle 54, in which they are coupled to an external connector 56, which may be a multiple pin connector. The connector 56 electrically couples the mapping electrodes 24 to the processing system 32. Further details on mapping systems and methods for processing signal generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are incorporated herein by reference.

It is noted that other multi-electrode structures could be deployed on the distal end of the mapping catheter 14. It is further noted that the multiple mapping electrodes 24 may be disposed on more than one structure rather than, for example, the single mapping catheter 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Although the mapping electrodes 24 have been described as being carried by dedicated mapping probes, such as the mapping catheter 14, the mapping electrodes may be carried on non-mapping dedicated probes or multifunction probes. For example, an ablation catheter, such as the ablation catheter 16, can be configured to include one or more mapping electrodes 24 disposed on the distal end of the catheter body and coupled to the signal processing system 32 and guidance system 38. As another example, the ablation electrode at the distal end of the ablation catheter may be coupled to the signal processing system 32 to also operate as a mapping electrode.

Figure 3:
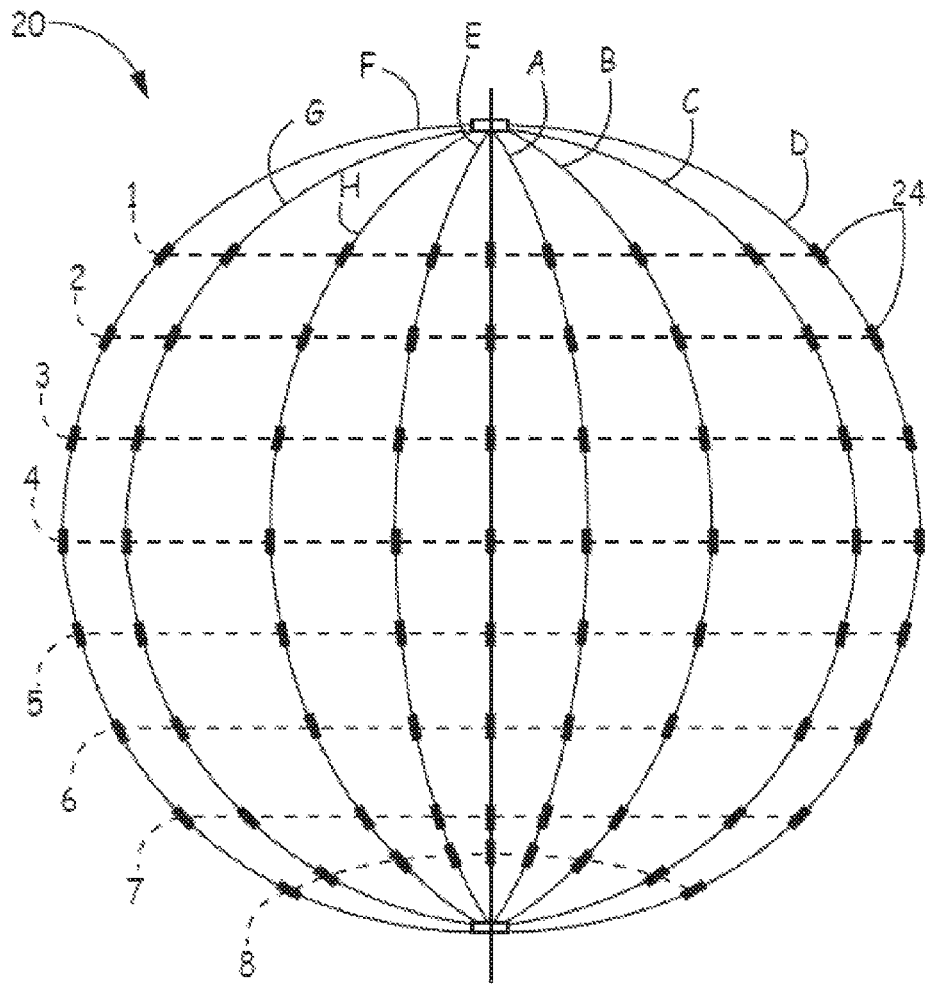
FIG. 3 is a schematic side view of an embodiment of the basket functional element including a plurality of mapping electrodes.

To illustrate the operation of the system 10, FIG. 3 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on a basket structure 20, the mapping electrodes 24 may alternatively be arranged in different numbers, on different structures, and/or in different positions. In addition, multiple basket structures can be deployed in the same or different anatomical structures to simultaneously obtain signals from different anatomical structures.

After the basket structure 20 is positioned adjacent to the anatomical structure to be treated (e.g., left atrium, left ventricle, right atrium, or right ventricle of the heart), the processing system 32 is configured to record the activation signals from each electrode 24 channel related to physiological activity of the anatomical structure, i.e. the electrodes 24 measure electrical activation signals intrinsic to the physiology of the anatomical structure. The activation signals of physiological activity can be sensed in response to intrinsic physiological activity or based on a predetermined pacing protocol instituted by at least one of the plurality of electrodes 24. The processing system 32 can be configured to determine a restitution curve based on a mutual information correlation between a previous diastolic interval (pDI) and an action potential duration and, similarly, between a previous diastolic interval and a conduction velocity of the anatomical structure. Alternatively, the processing system 32 can be configured to determine a restitution curve using a histogram based on a correlation between an action potential duration and a previous diastolic interval (pDI). A restitution curve can be useful for a physician when trying to identify or characterize a cardiac pathology, e.g. cardiac arrhythmia.

Figure 4:
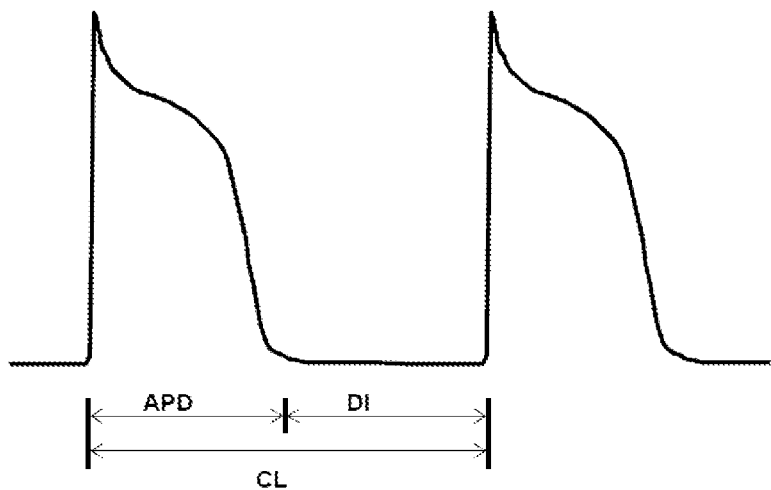
FIG. 4 is an illustration of an example of an action potential curve showing a cycle length including an action potential duration and a diastolic interval.

FIG. 4 Illustrates an action potential that includes the cycle length (CL), the duration between the activations of two consecutive beats, which is composed of an action potential duration (APD), i.e., the duration between the recovery and the activation of the same beat, and a diastolic interval (DI), i.e., the duration between the activation of the next beat and the recovery of the current beat. One factor that determines the APD is the preceding CL. When the CL is constant, the APD is constant. However, when the CL is shortened or lengthened, the proceeding APD is shortened or lengthened, respectively. The relationship between the changes in APD and the varying previous DI (pDI) is known as restitution. Restitution reflects the recovery properties of the anatomical structure, e.g. cardiac tissue, and has diagnostic importance to a physician.

Figure 5:
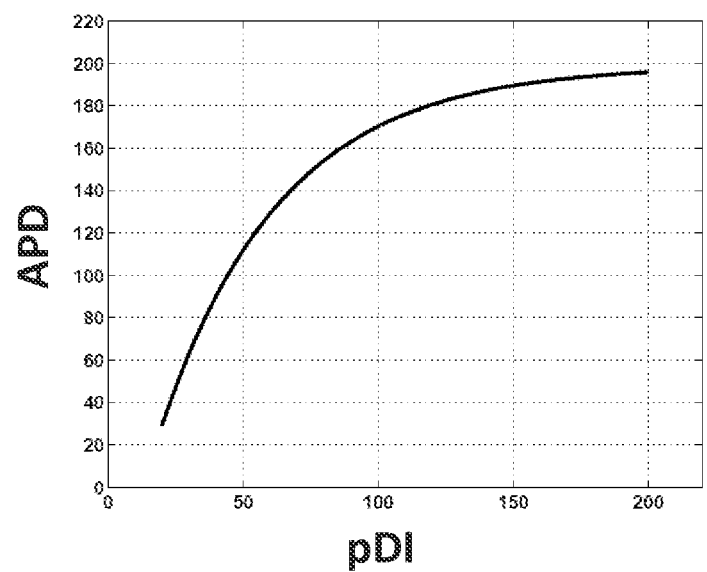
FIG. 5 is an illustration of an example of an action potential duration restitution curve.

As illustrated in FIG. 5, a restitution curve is a plot of the variation of APD with respect to pDI (or CL) and is important in understanding cardiac pathologies, such as aberrant signal conduction and/or fibrillation. Restitution curves can also be used to guide the insertion of action potential waveforms into activation signals to visualize activation signal propagation. An APD restitution curve is typically measured over a range of diastolic intervals and plotted to resemble or correspond to an exponential curve. Conventionally, to measure the APD for each corresponding DI, the DI is set constant via a cardiac pacing protocol to artificially generate the various Drs.

In some embodiments, the processing system 32 is configured to determine an APD restitution curve based on a functional relationship or association between the APD and pDI of the acquired action potentials. After the activation signals are recorded, the processing system 32 determines the cycle length of each activation signal and estimates the APD and DI for each cycle length. The initial estimate of APD and DI for each cycle length can be random or based on a priori information, such as a pre-determined restitution template or a previously determined restitution curve. The processing system 32 generates a two-dimensional restitution data set which pairs each estimated APD with an estimated pDI, i.e., an estimated DI from the directly preceding activation signal. The restitution dataset is plotted on two-dimensional coordinate plane to generate an initial restitution curve as illustrated in FIG. 5 where the x-axis is the pDI in milliseconds and the y-axis is the APD in milliseconds and thus each point on the restitution curve will be in the form of (pDI, APD). Since the initial restitution curve is based on the initial restitution dataset of estimated and/or arbitrarily chosen APD's and DI's, the initial restitution curve may not resemble the exponential curve illustrated in FIG. 5. However, if a priori knowledge is applied when estimating the initial APD and DI for each CL, the initial restitution curve may resemble an exponential curve typically characteristic of an APD restitution curve.

The processing system 32 determines a functional association between the two dimensions, i.e., the APD and the pDI, of the restitution data set. The functional association may include maximizing at least one of a mutual information, maximal information coefficient, and a distance correlation between the estimated action potential duration and the estimated diastolic interval from the preceding cycle length. Since the actual APD and DI for each CL of the recorded activation signals are unknown, the processing system 32 can estimate APD and DI using an iterative functional association. For example, the processing system makes iterative changes to optimize initial restitution dataset set until the functional association, i.e., a mutual information, maximal information coefficient, and a distance correlation, is maximized, at which point the resultant APD restitution curve from the optimized restitution dataset should resemble the illustrated exponential plot of FIG. 5.

A mutual information correlation quantifies the association or dependency between two variables, i.e. APD and pDI, without any assumption of functional form of the relationship between them. A maximal information coefficient is a measure of the strength of a linear or non-linear association between two variables X and Y, i.e. APD and pDI. Distance correlation is a measure of statistical dependence between two random variables or two random vectors, i.e. APD and pDI, of arbitrary, not necessarily equal dimension, and is usually derived from distance variance, distance standard deviation, and distance covariance.

Figure 6A:
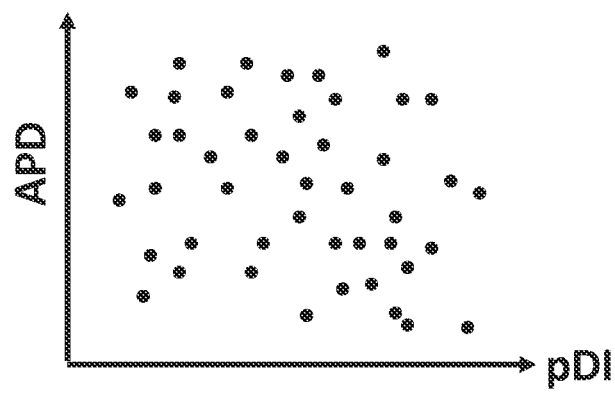
FIG. 6A is an illustration of an initial action potential restitution curve.
Figure 6B:
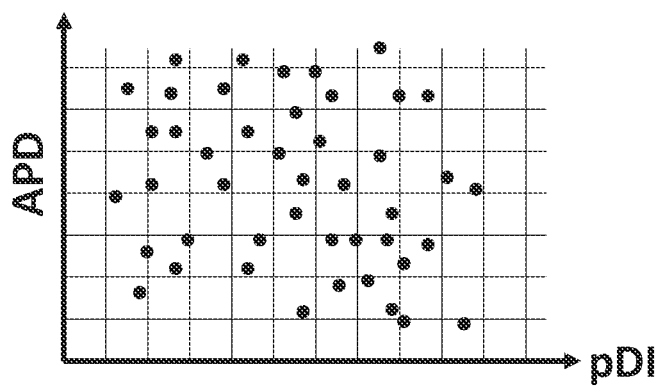
FIGS. 6B-6C are illustrations of the initial action potential restitution curve of FIG. 6A after segmentation.

To optimize the initial restitution dataset according to a functional association, the processing system 32 segments the initial restitution curve (FIG. 6A) into a grid having a plurality of grid locations as illustrated in FIG. 6B and an initial functional association is determined. The processing system 32 selects a grid location and moves the points from the selected grid location to each one of the six neighboring grid locations. Since a point of the restitution curve is represented by (pDI, APD), to move a point on the restitution curve the processing system 32 adjusts at least one of the estimated APD and pDI corresponding to that point such that the point is located in one of the neighboring grid locations. After the points are relocated to a neighboring grid location, the functional association is determined. If a positive change in the functional association is observed between the previous and current functional association, the changes are updated in the restitution dataset. In this manner, points within each grid location are relocated to neighboring grid location until the functional association at all grid locations for all grid relocations is maximized. The resultant restitution data set is an optimized restitution dataset consisting of optimized APD and pDI values.

Figure 6C:
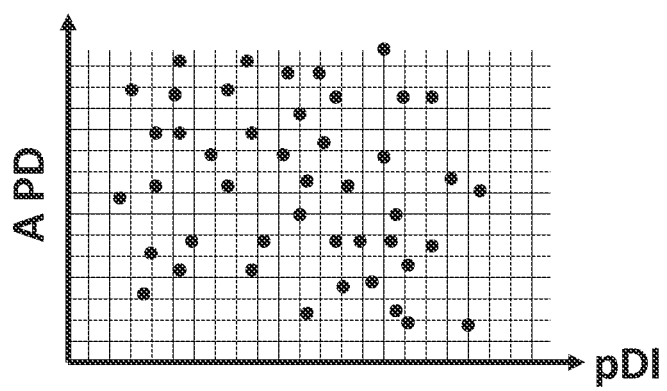

In some embodiments, to further optimize the restitution dataset and the corresponding estimated APD and pDI values, the resolution of the grid is increased, as illustrated in FIG. 6C, from a coarser resolution to a finer resolution and the iterative process of relocating points from one grid location to a neighboring grid location until the functional association is further maximized. For example, at a selected grid location, the processing system 32 relocates the points of the restitution dataset that lie within in the selected grid location to any one of the eight neighboring grid locations by adjusting the APD and pDI values associated with that point. A functional association is determined and then compared to the previous functional association. If a positive change in the functional association is observed, the changes are update in the restitution dataset. This process is repeated at each grid location for each corresponding neighboring grid location until the functional association is maximized.

In some embodiments, the restitution dataset is generated from a selected set of electrodes of the plurality of electrodes. The restitution dataset is optimized according to a functional association as previously described. The resultant optimized APD restitution curve is set as a predetermined restitution template and used as previously mentioned a priori knowledge for generating an optimized restitution dataset for a neighboring set of electrodes.

The a priori information can be used to maximize a similarity between the generated restitution data set and the predetermined restitution template. The similarity may include maximizing a correlation coefficient between the generated restitution curve and the predetermined restitution template or maximizing a mean square error between the generated restitution curve and the predetermined restitution template. The restitution template may include any one of a previously generated restitution template of the same patient or a different patient, a restitution curve generated from an adjacent or neighboring set of electrodes during the same study, a rising exponential function, and a sigmoidal function.

Figure 7A:
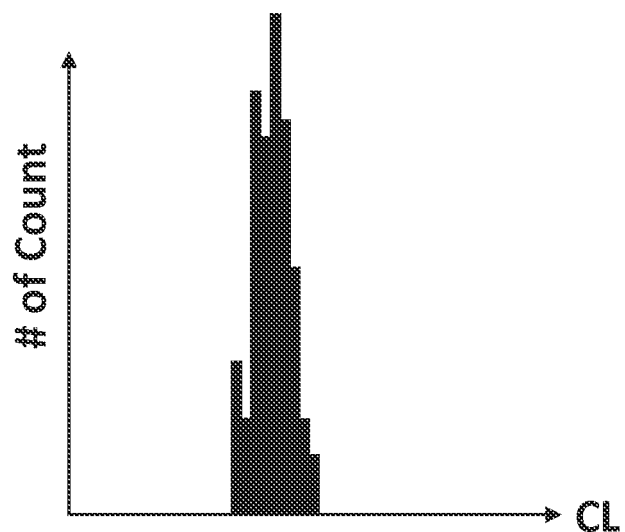
FIG. 7A is an illustration of an example of a cycle length histogram during paced or sinus rhythms.
Figure 7B:
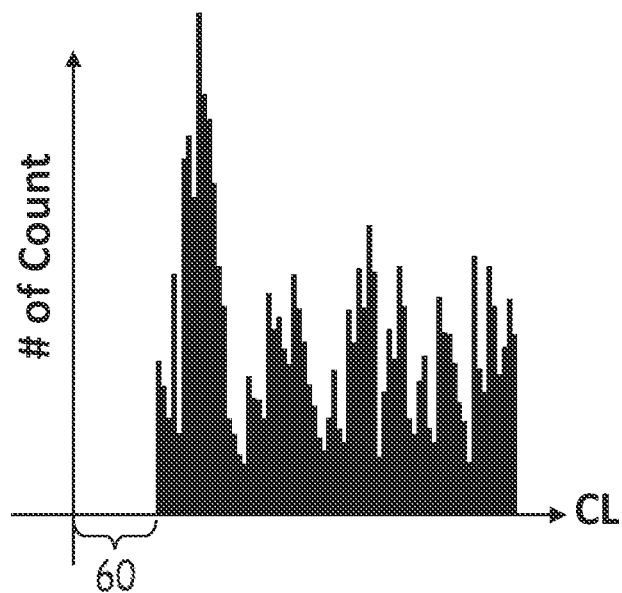
FIG. 7B is an illustration of an example of a cycle length histogram during atrial fibrillation.

In some embodiments, the processing system 32 is configured to determine a restitution curve based on a function of action potential duration and preceding cycle length. For example, the function may be a histogram correlation between an action potential duration (APD) and a previous cycle length (pCL). A typical histogram of a paced or sinus CL's is expected to be narrow as illustrated in FIG. 7A. However, a CL histogram during atrial fibrillation or a random pacing protocol can be wide, as illustrated in FIG. 7B. Given sufficient activation signal recordings, the lower tail of the histogram converges to zero due to a refractory period 60. The refractory period is a time interval after an action potential during which a new action potential cannot be elicited. This refractory period 60 can be used to estimate the APD of each cycle length, from which the corresponding DI and pDI can be estimated to generate an APD restitution curve of the recorded activation signals.

The processing system 32 senses the activation signals from the plurality of electrodes 24 and determines a cycle length (CL) for each activation signal. The activation signals of physiological activity can be sensed in response to intrinsic physiological activity or based on a predetermined pacing protocol instituted by at least one of the plurality of electrodes 24. A histogram of the determined CL's is generated based on the preceding cycle length. The processing system 32 determines the range of all CL's and segments the range into equidistance bins. For example, if the determined range is 110 millisecond (ms) to 500 ms, the processing system may generate bins of 5 ms intervals such as 110-115 ms, 115-120 ms, 120-125 ms, etc. However, this interval length can be shorter or longer. As previously described, an APD is dependent on the directly preceding DI, or pDI. The processing system identifies all sets of three consecutive activation signals and generates a histogram of cycle lengths for the second two activation signals for all triplets that share the same first cycle length bin. For example, for all triplets with a first cycle length that falls within the 110 ms-115 ms bin, the cycle length between second and third activation signals are histogrammed. The processing system 32 is configured to filter noise and outliers from the generated histograms with a smooth function such as, for example, a sigmoidal smoothing function.

The refractory period 60 is estimated based on the generated histograms. A region within the generated histograms between zero and a first bin with counts at least equal to a predetermined threshold is identified as the refractory period 60. The predetermined threshold count may be zero or a relative threshold based on a percentage of the count. The refractory period 60 is determined for all cycle length bins. The action potential duration for each bin is estimated according to the corresponding refractory period 60 and may be set to be duration of the corresponding refractory period.

For all previous cycle length pCL bins, i.e. 115-120 msec, 120-125 msec, etc., the process of generating a histogram, determining a refractory period from the generated histogram, and estimating the APD from the determined refractory period is repeated to obtain a plurality of (APD, pCL) data points, i.e. for all bins. The data points can be plotted to generate a function of APD and previous cycle length. For example, an APD vs. pCL curve can be generated according to the determined APD for each pCL bin. The processing system 32 partitions each determined CL into an APD and DI according to this function. The resultant APD's can be plotted against their corresponding preceding diastolic intervals to generate a restitution curve for the partitioned CL's.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for mapping an anatomical structure, the method comprising:
    sensing activation signals of physiological activity with a plurality of electrodes disposed in or near the anatomical structure, each activation signal having an associated cycle length;
    estimating an action potential duration and diastolic interval for each cycle length;
    generating an initial restitution curve based on the estimated action potential duration and diastolic interval from a preceding cycle length;
    iteratively optimizing each estimated action potential duration and corresponding diastolic interval to maximize a functional relationship between the estimated action potential duration and estimated diastolic interval from preceding cycle length; and
    generating a final action potential duration restitution curve based on the optimized action potential durations and diastolic intervals.

2. The method according to claim 1, wherein the step of estimating an action potential duration and diastolic interval includes randomly partitioning each cycle length to estimate the corresponding action potential duration and diastolic interval.

3. The method according to claim 2, wherein the step of iteratively optimizing each estimated action potential duration and corresponding diastolic interval, further includes:
    iteratively optimizing with a first partition resolution; and
    iteratively optimizing with a second partition resolution after optimizing with the first partition resolution, wherein the second partition resolution is higher than the first partition resolution.

4. The method according to claim 2, wherein the step of generating the restitution curve comprises:
    generating a two-dimensional dataset that pairs each estimated action potential duration with the estimated diastolic interval from a preceding cycle length; and
    plotting the two-dimensional dataset to generate an initial restitution curve.

5. The method according to claim 1, wherein the step of maximizing the functional relationship includes at least one of:
    maximizing a mutual information between the estimated action potential duration and estimated diastolic interval from preceding cycle length;
    maximizing a maximal information coefficient score the estimated action potential duration and estimated diastolic interval from preceding cycle length; and
    maximizing a distance correlation measure between the estimated action potential duration and estimated diastolic interval from preceding cycle length.

6. The method according to claim 1, further including maximizing a similarity between the generated restitution curve and a predetermined restitution template.

7. The method according to claim 6, wherein the step of maximizing the similarity includes at least one of:
    maximizing a correlation coefficient between the generated restitution curve and the predetermined restitution template; and
    minimizing a mean square error between the generated restitution curve and the predetermined restitution template.

8. The method according to claim 6, wherein the predetermined restitution template corresponds to any one of an exponential function, a sigmoidal function, and a previously generated optimized restitution curve.

9. The method according to claim 1, wherein the action potential duration restitution curve is generated for each of the plurality of electrodes.

10. The method according to claim 1, wherein the activation signals of physiological activity are sensed in response to a pre-determined pacing protocol instituted by at least one of the plurality of electrodes.

11. The method according to claim 1, and further comprising:
    generating an anatomical map of the anatomical structure based on the generated action potential duration restitution curve.

12. A method for mapping an anatomical structure, the method comprising:
    sensing cardiac activation signals with a plurality of electrodes disposed in or near the anatomical structure, each activation signal associated with a cycle length;
    partitioning each cycle length into an action potential duration and a diastolic interval;
    generating a restitution dataset such that each data point includes an action potential duration and a directly preceding diastolic interval;
    generating a two-dimensional plot of the data points, the plot having a predefined grid of discrete grid locations;
    determining a functional association within the restitution dataset;
    adjusting the partition of each cycle length such that each data point is shifted from one grid location to another grid location;
    repeating the adjusting and determining steps to maximize the functional association within the restitution data set; and
    generating an action potential duration restitution curve based on the restitution dataset corresponding to the maximized functional association.

13. The method according to claim 12, wherein the functional association includes at least one of:
    maximizing a mutual information between the estimated action potential duration and estimated diastolic interval from preceding cycle length;

maximizing a maximal information coefficient score the estimated action potential duration and estimated diastolic interval from preceding cycle length; and maximizing a distance correlation measure between the estimated action potential duration and estimated diastolic interval from preceding cycle length.

14. The method according to claim 12, wherein the functional association is based on maximizing a similarity between the generated restitution curve and a predetermined restitution template.

15. The method according to claim 14, wherein the similarity includes at least one of:

maximizing a correlation coefficient between the generated restitution curve and the predetermined restitution template; and minimizing a mean square error between the generated restitution curve and the predetermined restitution template.

16. The method according to claim 14, wherein the predetermined restitution template corresponds to any one of an exponential function, a sigmoidal function, and a previously generated optimized restitution curve.

17. The method according to claim 12, wherein after the functional association is maximized, the method further comprises:

increasing the resolution of the predefined grid; and repeating the adjusting and determining steps until the functional association is further increased across the entire restitution data set.

18. The method according to claim 12, wherein the cardiac activation signals are sensed in response to a pre-determined pacing protocol instituted by at least one of the plurality of electrodes.

19. The method according claim 18, wherein the predetermined pacing protocol includes at least one of random pacing pulses with inter-pulse intervals sampled from a statistical distribution.

20. The method according to claim 12, further comprising:

generating a cardiac map based on the generating action potential duration restitution curve.

21. A method for mapping an anatomical structure, the method comprising:

sensing activation signals of physiological activity with a plurality of electrodes disposed in or near the anatomical structure, each activation signal having an associated cycle length;

generating a function of action potential duration and preceding cycle length;

partitioning each cycle length into an action potential duration and a diastolic interval based on the generated function;

generating an initial action potential duration restitution curve based on the partitioned action potential duration and a preceding diastolic interval, wherein the initial action potential duration restitution curve represents a functional association between the action potential duration and a corresponding diastolic interval; and generating a final action potential duration restitution curve based on at least one of an adjusted action potential duration and an adjusted corresponding diastolic interval, wherein the final action potential duration restitution curve has a functional association that is more positive than the functional association of the initial action potential duration restitution curve.

22. The method according to claim 21, wherein the step of generating a function includes:

generating a histogram of the cycle length of each activation signal based on the preceding cycle length;

determining a refractory period of a cycle length based on the generated histogram;

estimating an action potential duration based on the determined refractory period; and repeating the steps of generating a histogram, determining the refractory period, and estimating the action potential duration for a plurality of preceding cycle length.

23. The method according to claim 22, wherein the step of generating a histogram includes:

determining the range of recorded cycle lengths;

segmenting the determined range into equidistance bins;

identifying all triplets of three consecutive activation signals; and generating a histogram of cycle lengths for a second and third activation signal for triplets that share a first cycle length bin.

24. The method according to claim 23, wherein the refractory period is determined for all cycle length bins.

25. The method according to claim 22, wherein the step of determining the refractory period includes:

identifying a region of the generated histogram between zero and a first bin with counts at least equal to a predetermined threshold; and determining the refractory period according to the identified region.

26. The method according to claim 25, wherein the estimated action potential duration is the duration of the refractory period.

27. The method according to claim 23, wherein the step of determining the refractory period includes:

fitting a smoothing function to the generated histogram; and identifying as the refractory period a region of the generated histogram between zero and where the smoothing function falls below a predetermined threshold.

28. The method according to claim 27, wherein the smoothing function is a sigmoidal smoothing function.

29. The method according to claim 21, wherein the activation signals of physiological activity are sensed in response to a pre-determined pacing protocol instituted by at least one of the plurality of electrodes.

30. The method according to claim 21, further comprising:

generating a cardiac map based on the generating action potential duration restitution curve.

* * * * *